(12) United States Patent
Jeannin et al.

(10) Patent No.: US 7,229,449 B2
(45) Date of Patent: Jun. 12, 2007

(54) DEVICE FOR FOLDING FLEXIBLE INTRAOCULAR IMPLANTS

(75) Inventors: Lionel Jeannin, Choisy (FR); Guy Vitally, Villaz (FR)

(73) Assignee: Corneal Industrie, Pringy (FR)

( * ) Notice: Subject to any disclaimer, the term of this patent is extended or adjusted under 35 U.S.C. 154(b) by 582 days.

(21) Appl. No.: 10/495,177

(22) PCT Filed: Nov. 28, 2002

(86) PCT No.: PCT/FR02/04081

§ 371 (c)(1),
(2), (4) Date: May 11, 2004

(87) PCT Pub. No.: WO03/045286

PCT Pub. Date: Jun. 5, 2003

(65) Prior Publication Data

US 2004/0199172 A1 Oct. 7, 2004

(30) Foreign Application Priority Data

Nov. 30, 2001 (FR) .................................. 01 15491

(51) Int. Cl.
*A61F 9/00* (2006.01)
(52) U.S. Cl. ..................... 606/107; 623/6.12; 206/438
(58) Field of Classification Search ................ 606/107; 623/6.12; 206/5.1, 438; 351/159

See application file for complete search history.

(56) References Cited

U.S. PATENT DOCUMENTS 5,702,400 A 12/1997 Brown et al.
6,007,542 A 12/1999 Duprat

FOREIGN PATENT DOCUMENTS

EP 0 923 914 A1 6/1999

*Primary Examiner*—Julian W. Woo
*Assistant Examiner*—Sarah Webb
(74) *Attorney, Agent, or Firm*—Cohen Pontani Lieberman & Pavane LLP

(57) ABSTRACT

The invention relates to a folding device for folding intraocular implants having flexible optical portions. Said device comprises two folding element facing each other and whose ends are connected together by deformable means. Each folding element comprises a body and a jaw projecting from said body, an elastically deformable support projecting from said body in the direction in which the two elements are brought together, a positioning stud projecting from said second end of the support perpendicularly to said support and facing upwards so as to co-operate, at rest, with the periphery of the optical portion of the implant, and an extension projecting from said body in the direction in which the two elements are brought together, and having a ramp suitable for co-operating with the support on the other folding element while the two folding elements are being brought together to cause said positioning stud to be lowered.

5 Claims, 2 Drawing Sheets

DEVICE FOR FOLDING FLEXIBLE INTRAOCULAR IMPLANTS

This is a U.S. national stage of application No. PCT/FR02/04081, filed on 28 Nov. 2002. Priority is claimed on that application and on the following application: Country: France, Application No.: 0115491, Filed: 30 Nov. 2001.

BACKGROUND OF THE INVENTION

1. Field of the Invention

The present invention relates to a device for folding a flexible intraocular implant of which at least an optical portion is made of a flexible material.

More precisely, the invention relates to a device of the pincer type that enables the optical portion of an intraocular implant to be folded automatically, the optical portion being made of a biocompatible flexible material such as a material selected from silicones, hydrophobic acrylics, and hydrophilic acrylics (poly-hydroxyethyl methacrylates (pHEMAs)).

2. Discussion of Related Art

It is known that one of the main advantages of making the optical portion of an intraocular implant out of a flexible material is that it is then possible for said optical portion (which is usually circular or substantially circular) to be folded about a diameter before the resulting folded implant is inserted inside the eye so as to be put in place on the desired internal portion of the eye. It can be understood that, since the optical portion, which can have a diameter of about 6 millimeters (mm) is folded before it is inserted in the eye, the incision that needs to be made in the cornea in order to put the implant in place in this way can be of small size, typically about 3 mm to 4 mm. This situation is particularly advantageous because it is known that, when the incision to be made in the cornea is small in size, the incision heals under good conditions, thereby making it possible to reduce the period of convalescence very significantly.

Naturally, since the implant is transparent and since it is relatively small in size because the diameter of the optical portion is usually about 6 mm, it can be understood that it is relatively difficult to fold said optical portion using conventional surgical instruments. Therefore, mechanical devices have been designed that are capable of performing such folding automatically.

Folding devices are of two types. In a first type, the folding device is in the form of a sort of pair of pincers that has two jaws between which the optical portion of the implant to be folded is placed. Bringing the two jaws towards each other causes the optical portion to be folded, and the surgeon then merely has to take hold of the folded optical portion with suitable forceps.

The second type of folding device can be referred to as an "implant injector" and makes it possible, in a first stage, for the optical portion of the implant to be folded automatically, and in a second stage, for the folded implant to be inserted into the eye by means of a hollow needle with a piston for pushing the folded implant into the needle, it being possible to insert the needle into the incision made in the cornea.

The present invention relates to the first type of implant-folding device, i.e. to the pincer type.

Numerous implant-folding devices of the pincer type, i.e. of the above-described type, are already known. Unfortunately, such known devices suffer from the drawbacks of not usually enabling the optical portion of the implant to be held correctly during the folding operation, and of not enabling the optical portion to be angularly positioned relative to the folding system.

OBJECTS AND SUMMARY OF THE INVENTION

An object of the present invention is to provide a folding device that ensures that the optical portion of the implant is positioned correctly during the folding operation.

In order to achieve this object, according to the invention, the folding device for folding an intraocular implant of which at least the optical portion is made of a flexible material comprises two folding elements facing each other and whose ends are connected together by deformable means making it possible for the two folding elements to be brought towards each other manually, each folding element comprising a body and a jaw projecting from said body and suitable for receiving a portion of the periphery of said optical portion and for supporting said implant. The device is characterized in that each folding element further comprises:

an elastically deformable support projecting from said body in the direction in which the two elements are brought together, and having a first end secured to the body and a second end;

a positioning stud projecting from said second end of the support perpendicularly to said support and facing upwards so as to co-operate, at rest, with the periphery of the optical portion of the implant; and an extension projecting from said body in the direction in which the two elements are brought together, and having ramp-forming means suitable for co-operating with the support on the other folding element while the two folding elements are being brought together to cause said positioning stud to be lowered relative to the plane defined by the two jaws by means of said support deforming elastically.

It can be understood that, by means of the presence of the two positioning studs, it is possible for the periphery of the flexible optical portion of the implant to be positioned correctly and held correctly during the folding operation. Furthermore, by means of the positioning studs retracting automatically and progressively while the two jaws of the folding device are being brought towards each other, said positioning studs do not interfere with operation of the device, and thus do not impede proper folding.

In an improved embodiment of the implant folding device, said folding device further comprises:

an additional elastically deformable support projecting from the body of one of the folding elements and having, at its free end, a guide member for guiding the folding direction, said member projecting upwards relative to said additional support and, at rest, being disposed below the plane defined by said jaws; and an additional extension projecting from the body of the other folding element and having first ramp-forming means and second ramp-forming means suitable for co-operating successively with said additional support so as firstly to cause the implant folding direction guide member to rise between said jaws above the plane defined by said jaws, and then to cause said folding direction guide member to return to its initial position.

It can be understood that this improved embodiment of the folding device makes it possible to define the direction in which the implant is folded, i.e. to force said implant to fold "upwards" when the device is in the normal in-use position. The folding direction guide member progressively rising along a diametral direction of the optical portion initially imparts the direction in which the optical portion folds and thus the direction of the folding that is ultimately obtained. In addition, because of the presence of the two ramps, the folding direction guide member retracts gradually after the folding direction has been imparted so that the presence of said guide member does prevent the optical portion of the implant from folding fully.

BRIEF DESCRIPTION OF THE DRAWINGS

Other characteristics and advantages of the invention will appear more clearly on reading the following description of embodiments of the invention given by way of non-limiting example. The description refers to the accompanying drawings, in which.

DETAILED DESCRIPTION OF THE PRESENTLY PREFERRED EMBODIMENTS

A first embodiment of the implant-folding device of the pincer type is described below with reference firstly to FIGS. 1 to 3.

Figure 1:
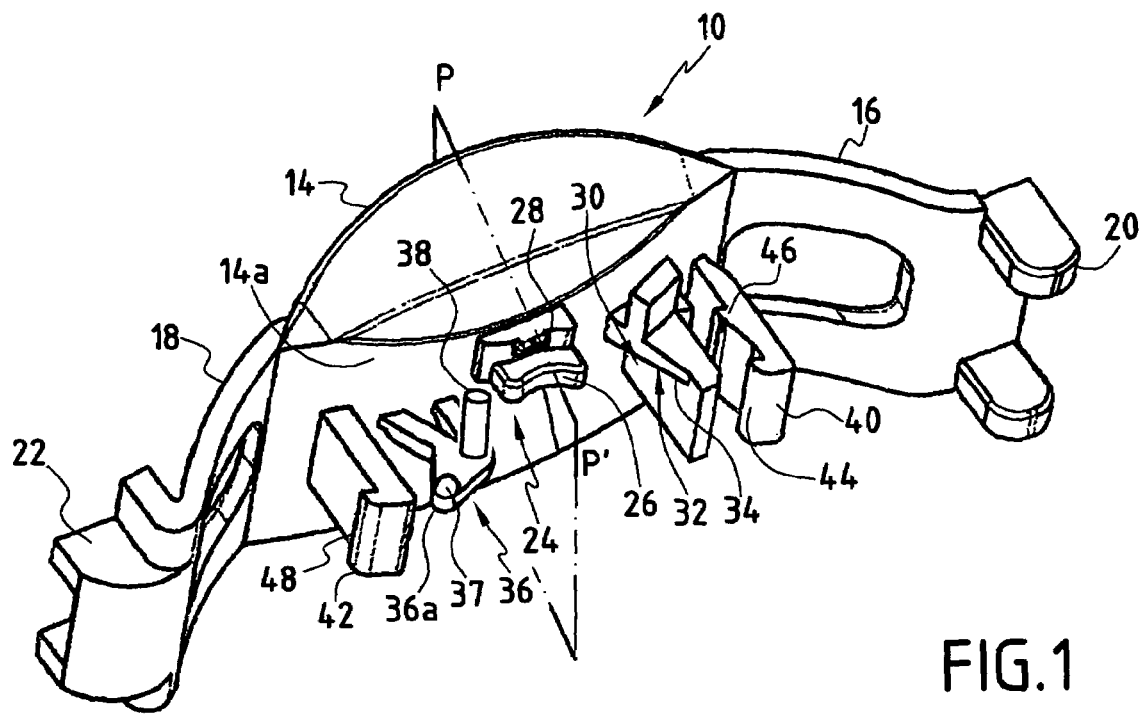
FIG. 1 is a perspective view of one folding element in a first embodiment of the folding device.
Figure 2:
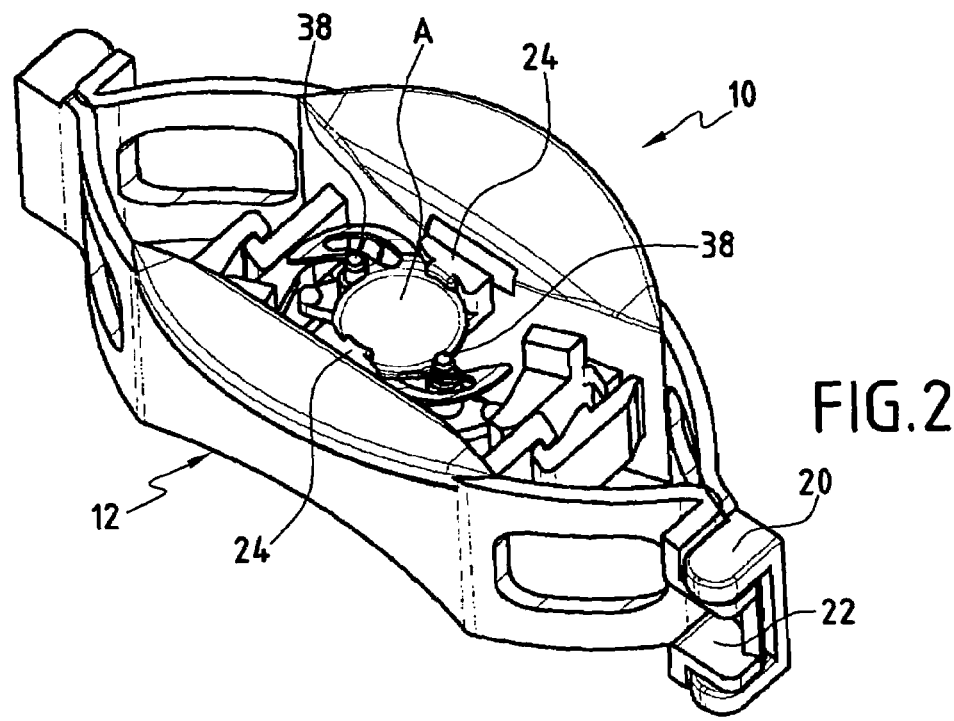
FIG. 2 shows the two folding elements as assembled together in the first embodiment.

As shown more clearly in FIG. 2, the folding device is made up of two folding elements respectively referenced 10 and 12 and which are identical in the first embodiment. Therefore, only the folding element 10 shown in FIG. 1 is described in detail below.

The folding element 10 has a central body 14 that is relatively bulky and relatively non-deformable. The body 14 is extended at each of its ends by wings 16 and 18 that are elastically deformable. The wings 16 and 18 are terminated by lugs 20 and by complementary bearing surfaces 22 making it possible for the two folding elements 10 and 12 to be secured together, at least temporarily.

In its midplane P, P', the body 14 has a jaw 24 that projects from the inside face 14a of the body. The jaw 24 is constituted by an implant support element 26 for supporting the implant, and by a top extension 28, the support element 26 and the top extension 28 defining a substantially dovetail shaped profile in which a portion of the periphery of the optical portion of the implant to be folded can be engaged. On one side of the jaw 24 a second extension 30 projects from the face 14a of the body 14, which extension is substantially non-deformable. A side portion 32 of the extension 30 defines a guide ramp 34 facing downwards and which slopes downwards going towards the face 14a of the body 14. On the other side of the jaw 24, a third extension 36 is provided that also projects from the face 14a of the body 14 and that constitutes an arm that is elastically deformable relative to the body 14. In the vicinity of its free end 36a, the arm 36 is provided with a portion 37 for co-operating with the ramp 34 on the other folding element. The arm 36 is also provided with a positioning stud 38 that extends upwards relative to the folding device as in its in-use position, i.e. in its position shown in FIG. 2. The extension 30, and more precisely its ramp-forming portion 34, and the arm 36 are disposed such that the extension 30 on one folding element is disposed facing the arm 36 on the other folding element so that, when the bodies 14 of the two folding elements are caused to move closer together by elastically deforming the branches 16 and 18, the ramp 34 co-operates with the portion 37 of the arm 36 so as to cause said arm to be lowered progressively, thus simultaneously causing the positioning stud 38 to be lowered.

As shown more clearly in FIG. 2, in the initial position, the optical portion A of the implant is properly positioned relative to the folding device by means of the two jaws 24 and by means of the two positioning studs 38. When the two bodies 14 of the folding elements are brought towards each other, the resulting bringing together of the jaws 24 causes the optical portion of the implant to be folded about its diameter that is perpendicular to the direction in which the jaws are brought together. Simultaneously, the ramps 34 cause the positioning studs 38 to be lowered, thereby making it possible, by means of them being retracted, for the optical portion of the implant to be folded fully.

On either side of the system constituted by the jaws, by the extension 30, and by the arms 36, FIG. 1 also shows resilient clipping tabs 40 and 42. The first clipping tab 40 is provided with two clipping catches, respectively referenced 44 and 46, while the clipping element 42 is provided with a single catch 48. The clipping elements of the two folding elements as disposed facing each other make it possible to define a first relative position for the folding elements by means of the clipping catches 44 and 48 co-operating. They also make it possible to define a second relative position for the folding elements by means of the clipping catches 46 and 48 co-operating. In the second position, the optical portion of the implant has been folded completely. In said second position, the optical portion of the implant can thus be held in the folded position while the surgeon takes hold of the folded optical portion of the implant by means of forceps.

Figure 3:
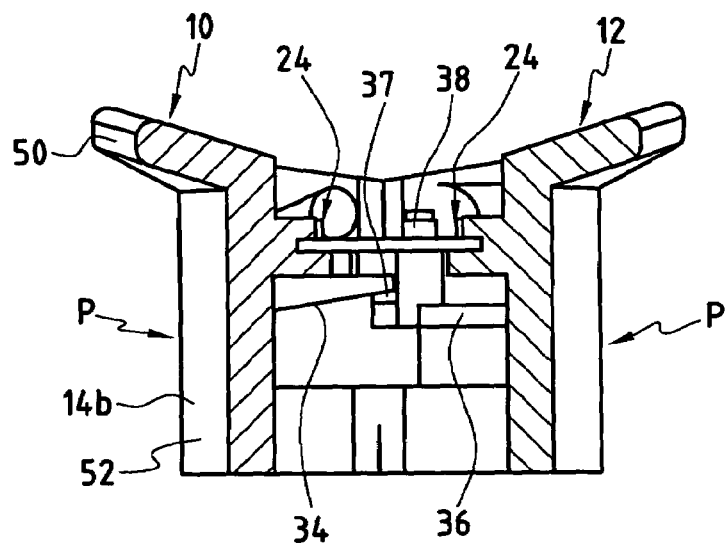
FIG. 3 is a view in section on the plane III—III of FIG. 2, showing how the positioning stud co-operates with the ramp to cause said ramp to be lowered.

As shown more clearly in FIG. 3, the outside face 14b of the body 14 of each of the folding elements has a top portion that forms a sort of collar 50, and a main portion 52 set back therefrom and that is substantially in the shape of a sector of a cylinder. In order to bring the two folding elements towards each other, the operator places fingers on the surfaces 52 under the collars 50 as indicated by arrows P. It is thus possible manually to cause the two folding elements 10 and 12 to come towards each other until the optical portion of the implant is folded.

Figure 4A:
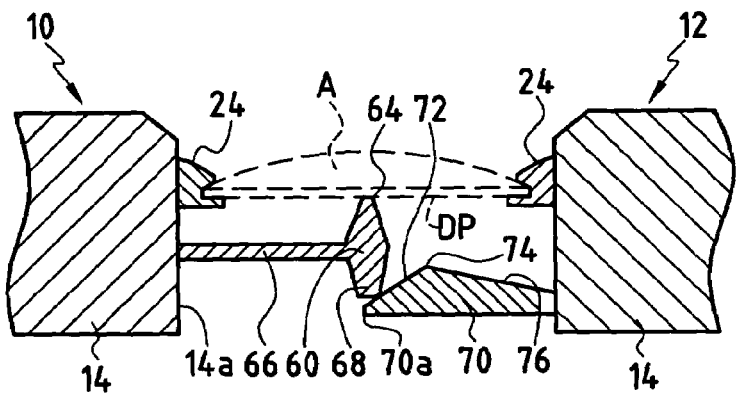
FIG. 4A is an overall view in vertical section, showing the entire folding device in an improved embodiment.
Figure 4B:
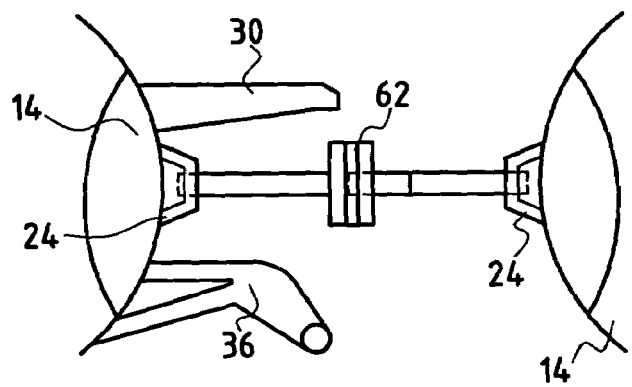
FIG. 4B is a plan view of the folding device shown in FIG. 4A.

Naturally, it is necessary for the folding of the optical portion to take place upwards so that the surgeon can take hold of the folded optical portion conveniently using forceps. However, it is to be feared that, under certain circumstances, folding of the optical portion might take place downwards. In order to avoid this risk, in a preferred embodiment of the folding device, said folding device can preferably include a guide member for guiding the direction in which the implant is folded, which member is shown in FIGS. 4A and 4B.

The direction in which the implant is folded is defined by a guide member 60 which is substantially V-shaped 62 having one edge 64 in the form of a ridge. The elastically deformable arm 66 extends in the midplane P, P' of the body 14 of the folding element 10. The length of the arm 66 is such that the ridge 64 of the guide member is disposed along a diameter of the optical portion A when the two folding elements are in their initial relative position in which the periphery of the optical portion is engaged in the jaws 24.

Naturally, the guide member 60 faces upwards relative to the in-use position of the device, and its ridge is disposed under the support 26 of the jaws 24. The guide member 60 is extended by a heel 68 which extends downwards.

The folding element 12 is provided with an extension 70 that projects from the face 14a of the body 14 of the other folding element 12 and in the midplane thereof so that, while the two folding elements are being brought together, the extension 70 can co-operate with the heel 68 of the guide member 60. In the vicinity of its free end 70a, the top face of the extension 70 defines a first ramp 72 which slopes upwards from the free end 70a to a ridge 74. That extension 70 has a second ramp 76 that slopes downwards from the ridge 74 towards the face 14a of the body 14 of the folding element. The ramps 72 and 76 are defined such that, in the first portion of the stage during which the two folding elements are brought together, the ramp 72 causes the ridge 64 of the guide element 60 to be raised progressively. The ridge 64 acts on the bottom face DP of the optical portion A of the implant, thereby forcing it to fold upwards. Once the heel 68 passes beyond the ridge 74 separating the ramps 72 and 76, the ramp 76 makes it possible for the guide member 60 to be lowered progressively, so that it returns to its initial vertical position. During the second portion of the bringing-together stage, the guide member 60 being lowered enables it to be retracted, thereby allowing the optical portion of the intraocular implant to be folded in full.

The invention claimed is:

1. A folding device for folding an intraocular implant of which at least the optical portion is made of a flexible material, said folding device comprising two folding elements facing each other and whose ends are connected together by deformable means making it possible for the two folding elements to be brought towards each other manually, each folding element comprising:
    a body and a jaw projecting from said body for receiving a portion of the periphery of said optical portion and for supporting said implant
    an elastically deformable support projecting from said body in the direction in which the two elements are brought together, and having a first end secured to the body and a second end;
    a positioning stud projecting from said second end of the support perpendicularly to said support and facing upwards so as to co-operate, at rest, with the periphery of the optical portion of the implant; and
    an extension projecting from said body in the direction in which the two elements are brought together, and having ramp means for co-operating with the support on the other folding element while the two folding elements are being brought together to cause said positioning stud to be lowered relative to the plane defined by the two jaws by means of said support deforming elastically.

2. A folding device according to claim 1, wherein said supports and said extensions are disposed on either side of said jaws.

3. A folding device according to claim 1 further comprising:
    an additional elastically deformable support projecting from the body of one of the folding elements and having, at its free end, a guide member for guiding the folding direction, said member projecting upwards relative to said additional support and, at rest, being disposed below the plane defined by said jaws; and
    an additional extension projecting from the body of the other folding element and having first ramp means and second ramp means suitable for co-operating successively with said additional support so as firstly to cause the implant folding direction guide member to rise between said jaws above the plane defined by said jaws, and then to cause said folding direction guide member to return to its initial position.

4. A folding device according to claim 3, wherein said additional support is disposed below the jaw on one of said folding elements, and the additional extension is disposed below the jaw on the other folding element.

5. A device according to claim 1 further comprising clipping means comprising a first clipping member secured to or integral with one of the folding elements and a second clipping member secured to or integral with the other folding element, said clipping members being suitable for defining a first relative position for the bodies of the folding elements, in which first position the optical portion of the implant is held between the jaws without being folded, and a second relative position in which said optical portion is folded.

* * * * *